US00PP20982P2

(12) United States Plant Patent
Cho

(10) Patent No.: US PP20,982 P2
(45) Date of Patent: May 11, 2010

(54) ***COLOCASIA* PLANT NAMED 'PINEAPPLE PRINCESS'**

(50) Latin Name: *Colocasia esculenta*
Varietal Denomination: PINEAPPLE PRINCESS

(76) Inventor: John Cho, P.O. Box 269, 424 Maune Pl., Kula, HI (US) 96790

( * ) Notice: Subject to any disclaimer, the term of this patent is extended or adjusted under 35 U.S.C. 154(b) by 232 days.

(21) Appl. No.: 12/006,581

(22) Filed: Jan. 4, 2008

(51) Int. Cl.
*A01H 5/00* (2006.01)

(52) U.S. Cl. ..... Plt./373

(58) Field of Classification Search ..... Plt./373, Plt./226, 263.1
See application file for complete search history.

*Primary Examiner*—Kent L Bell

(57) ABSTRACT

A new cultivar of *Colocasia* plant named 'PINEAPPLE PRINCESS' that is characterized by a combination of a large yellow-green colored leaves with light purple veins, a matte finish, undulating purple leaf margins, burgundy colored petioles and a small to medium sized compact plant. In combination these characteristics distinguish 'PINEAPPLE PRINCESS' from all other varieties of *Colocasia* known to the inventor.

5 Drawing Sheets

Genus: *Colocasia.*
Species: *esculenta.*
Denomination: 'Pineapple Princess'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'PINEAPPLE PRINCESS'. 'PINEAPPLE PRINCESS' is one of five applications by the inventor relating to new cultivars of *Colocasia.* The other four applications are titled *Colocasia* plant named 'Hawaiian Eye' (U.S. Plant Pat. No. 19,884), *Colocasia* plant named 'Blue Hawaii' (U.S. Plant Pat. No. 20,003), *Colocasia* plant named 'Diamond Head' (U.S. Plant Pat. No. 19,939) and *Colocasia* plant named 'Hilo Bay' (U.S. Plant Pat. No. 20,108).

*Colocasia* is a tuberous rooted perennial which is native to tropical Asia and Polynesia. It grows to 1.5–2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'PINEAPPLE PRINCESS' is the product of a formal breeding program carried out in a cultivated area in Kula, Hi. The purpose of the breeding program is to develop new commercial varieties by combining attributes not found in currently commercially available varieties.

'PINEAPPLE PRINCESS' is a seedling selection from the controlled pollination between the female parent variety '2001-52' (unpatented) and male parent breeding line '2002-41' (unpatented). Initially designated as '2004-39', 'PINEAPPLE PRINCESS' was derived as a single plant selected in 2004.

The new variety 'PINEAPPLE PRINCESS' has large yellow-green colored leaves with purple veins on the upper and lower leaf surface, a matte finish, and undulating purple leaf margins. 'PINEAPPLE PRINCESS' produces burgundy colored petioles. The leaves are ⅓ to ½ times larger than its male parent and 2 to 3 times larger than its female parent. The male parent, '2002-41', exhibits greenish-purple colored leaves with a matte finish, a smooth margin, and light purple venation. The petioles are dark purple in color with a matte finish. The female parent, '2001-52' exhibits smaller violet leaves with a purple spot on the upper leaf surface at the point of leaf and petiole attachment and a undulating margin. In these aspects, this new variety differs from its parents.

The closest comparison variety known to the inventor is 'Ruffles' (unpatented), its closest commercial variety. PINEAPPLE PRINCESS produces light yellow-green leaves with light purple veins and an undulating purple leaf margin compared to 'Ruffles' which exhibits a green leaf with an undulating leaf margin. PINEAPPLE PRINCESS produces a uniform burgundy colored petioles compared with 'Ruffles' that exhibit green petioles. PINEAPPLE PRINCESS produces a uniform compact plant compared with the tall 'Ruffles' plant.

The most commonly employed means of asexual propagation of the genus *Colocasia* is the excision and replanting of a shoot which consists of the apical 1 cm–2 cm portion of the plant corm with the attached basal 15 cm–20 cm portion of the petiole. In regions of the world where *Colocasia* is grown, this plant shoot is known as a "huli", and the means of propagation is known as "huli propagation". Asexual propagation of hulis of 'PINEAPPLE PRINCESS' began in 2004 in Hawaii by the inventor using huli propagation whereby the apical shoots are separated from the plant by cutting the shoot at the top of the corm immediately above the newest leaf scar and planted. Evaluation in field and pot studies have shown the unique features of 'PINEAPPLE PRINCESS' to be stable, uniform, and reproduces true to type in successive generations of asexual propagation.

SUMMARY OF THE INVENTION

The following traits have been repeatedly observed and represent the distinguishing characteristics of the new *Colocasia* variety named 'PINEAPPLE PRINCESS'. In combination these traits set 'PINEAPPLE PRINCESS' apart from all other varieties of *Colocasia* known to the inventor. 'PINEAPPLE PRINCESS' has not been tested under all possible conditions and phenotypic differences may be observed with variations in environmental, climatic and cultural conditions, however, without any variance in genotype:

1. 'PINEAPPLE PRINCESS' exhibits large saggitate-shaped leaves with purple veins and undulating purple margins.
2. The leaves of 'PINEAPPLE PRINCESS' are yellow-green in color.
3. The surface of the leaves of 'PINEAPPLE PRINCESS' is a matte finish.
4. 'PINEAPPLE PRINCESS' has burgundy colored petioles.
5. 'PINEAPPLE PRINCESS' produces a small to medium sized compact plant.

BRIEF DESCRIPTION OF THE DRAWINGS

The accompanying color drawings

Figure 1:
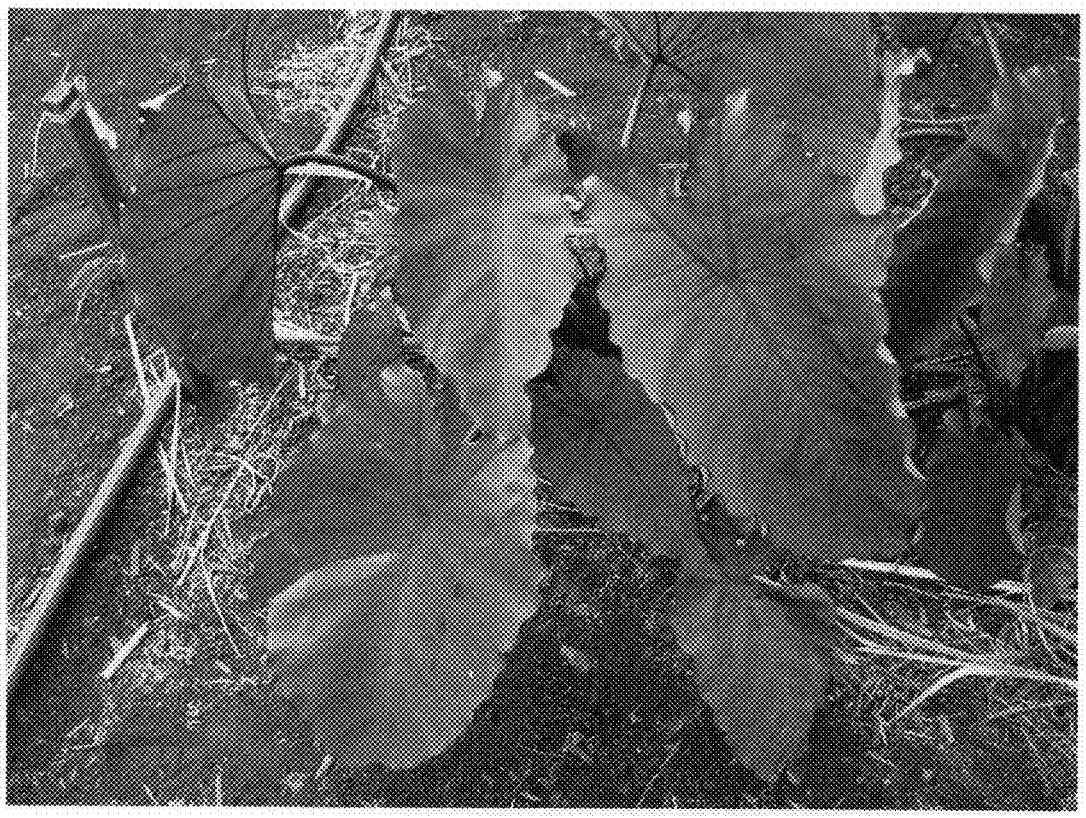
FIGS. 1 to 5 illustrate the overall appearance of 'PINEAPPLE PRINCESS' showing the colors as true as it is reasonably possible to obtain in colored reproductions of this type. Colors in the drawing may differ from the color values cited in the detailed botanical description, which accurately describe the actual colors of the new variety 'PINEAPPLE PRINCESS'.

The drawing labeled as FIG. 1 shows 'PINEAPPLE PRINCESS' grown from a huli after approximately 5 months.

Figure 2:
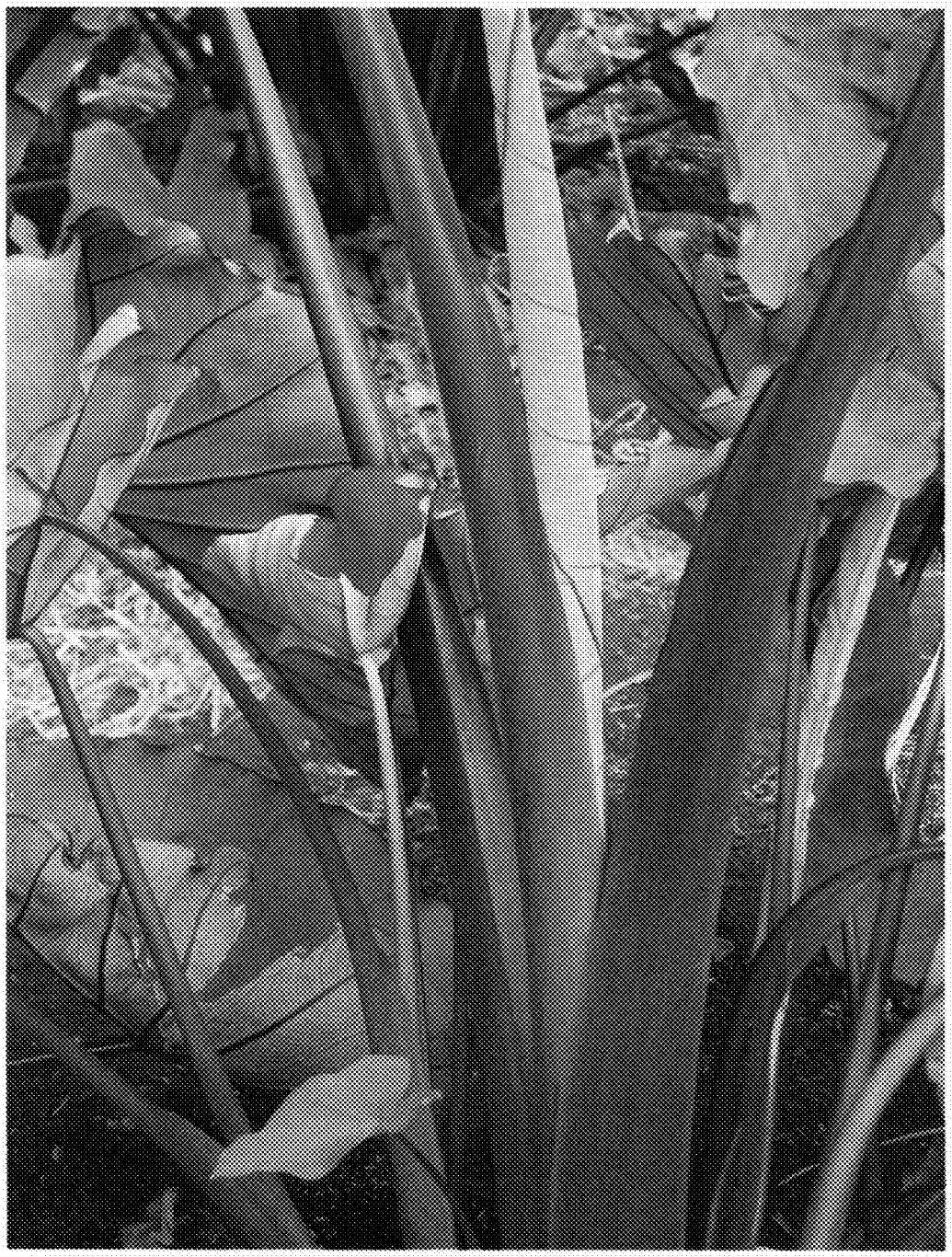

The drawing labeled as FIG. 2 shows the burgundy colored petioles of 'PINEAPPLE PRINCESS'.

Figure 3:
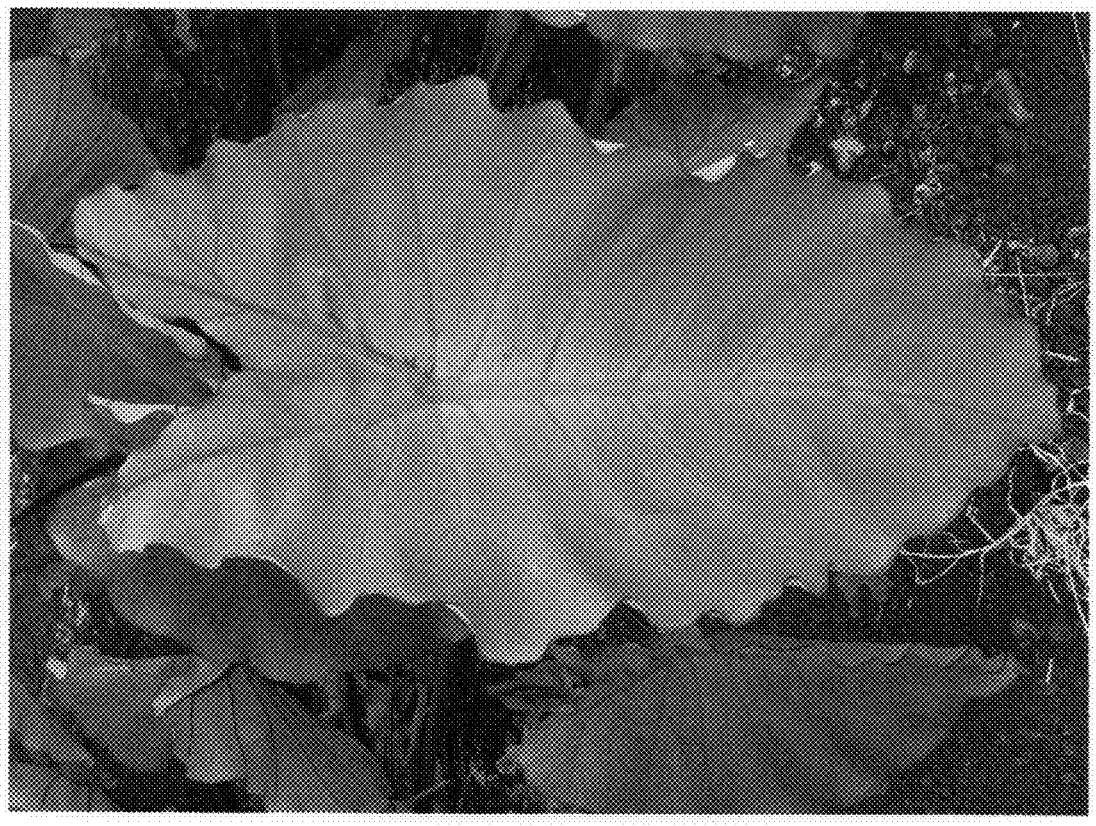

The drawing labeled FIG. 3 illustrates a sagittate 'PINEAPPLE PRINCESS' mature leaf blade. Lamina is yellow-green with purple veins and purple undulating margins on the adaxial surface.

Figure 4:
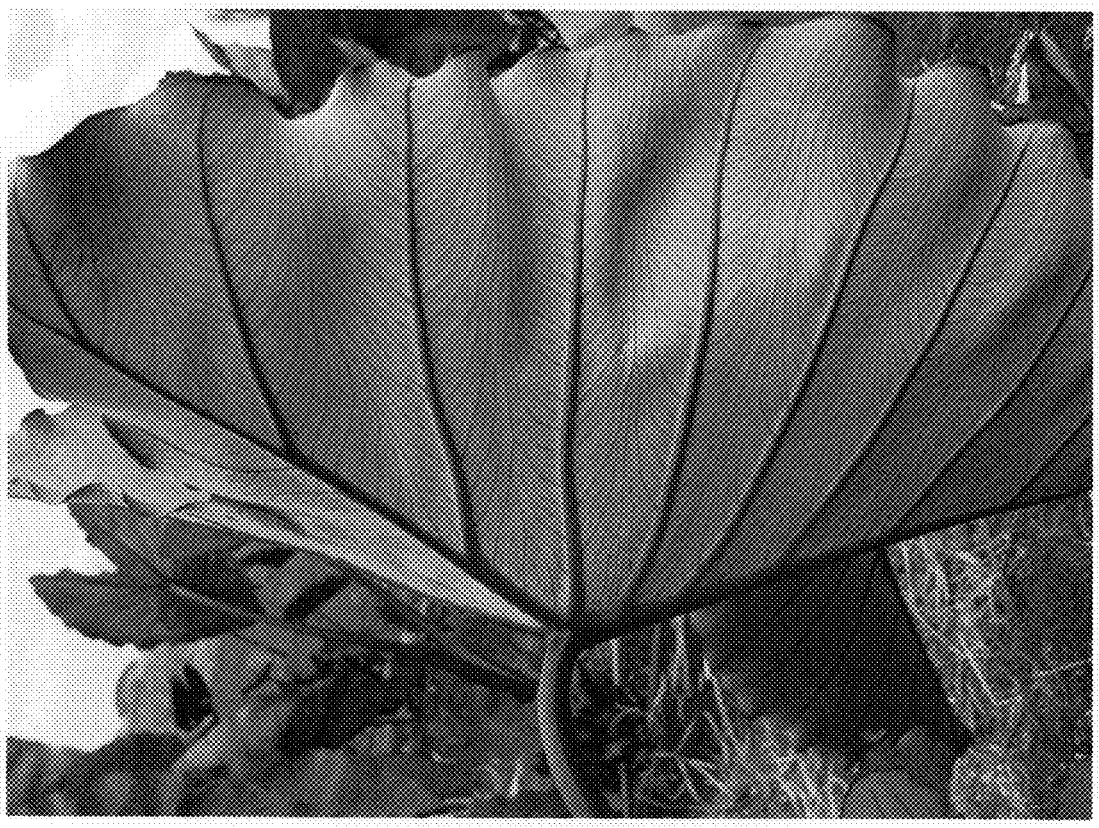

The drawing labeled as FIG. 4 shows the underside of a mature leaf of 'PINEAPPLE PRINCESS' with the light purple lamina and purple venation.

Figure 5:
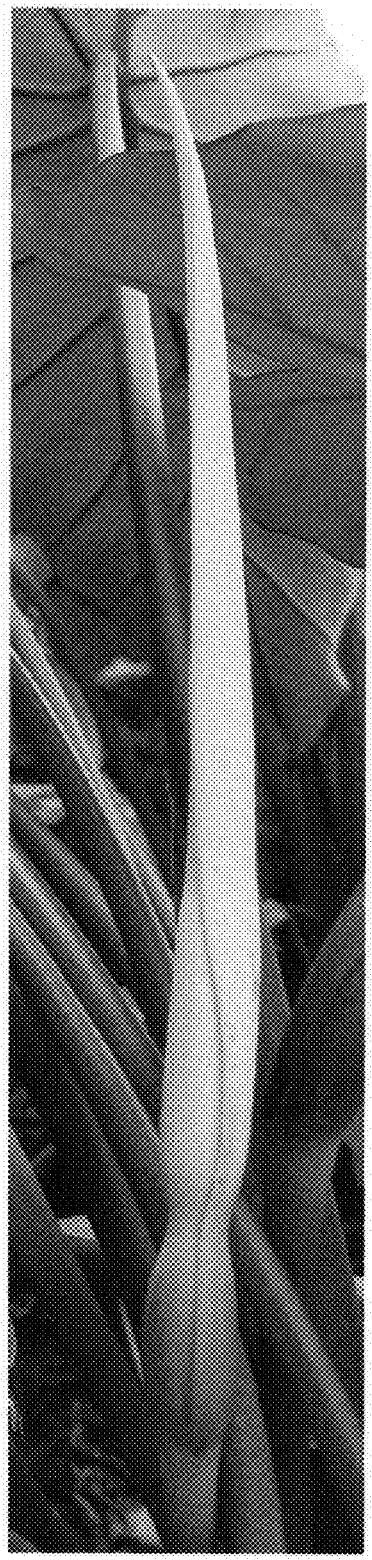

The drawing labeled as FIG. 5 shows the sheath or spathe that normally encloses the spadix of 'PINEAPPLE PRINCESS'.

Figure 6:
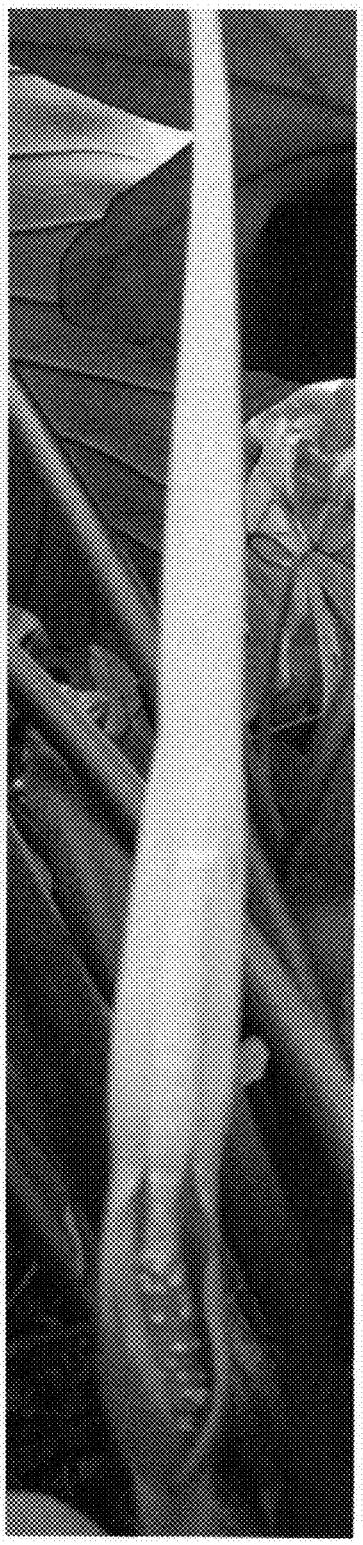

The drawing labeled as FIG. 6 shows the inflorescence or spadix of 'PINEAPPLE PRINCESS'.

All drawings have been made from plants which were approximately 5 months old from a division and which have been grown out-of-doors. No growth regulators have been applied.

BOTANICAL DESCRIPTION OF THE PLANT

The following is a detailed description of the new *Colocasia* plant named 'PINEAPPLE PRINCESS'. Data was collected from plants that were 3–6 months of age grown outside in Kula, Hi. as indicated. The color determinations are in accordance with the 2001 edition of The Royal Horticultural Society Colour Chart, London, England, except where general color terms of ordinary dictionary significance are used. The growing requirements are similar to other *Colocasia*.

Botanical classification:

Genus: *Colocasia*

Species: *esculenta*

Denomination: 'PINEAPPLE PRINCESS'

Common name: Taro or elephant ears.

Plant use: Food, container or landscape plant.

Cultural requirements: Cultural requirements are well draining soil or growing media, full sun to partial shade.

Root system: Fibrous.

Plant vigor: Vigorous.

Plant growth rate: Rapid. Once rooted, plants become saleable in 1-gallon containers in 6 weeks.

Parentage:

*Female parent.*—'2001-52'.

*Male parent.*—'2002-41'.

Plant description: The plant has 5 to 9 suckers closely attached to the mother plant. A "mother plant" is the plant material which is first introduced into the soil to begin production. Typically, this plant material contains part of the huli and 2–3 leaf blades. This produces a "mother corm" which produces lateral shoots called 'cormels' which give rise to daughter plants. Daughter plants begin to appear above soil level about 2–3 months after planting of the mother plant.

Plant dimensions: 55 cm to 80 cm in height and 100 cm to 120 cm in width.

Plant hardiness: USDA Zone 7

Propagation: Propagation is accomplished by huli propagation and by tissue culture.

Huli propagation: Root formation occurs immediately after transplanting. Propagation is complete when fully rooted. Daughter plants appear above soil level around 2–3 months after huli planting.

Tissue culture: Time to develop a new plant capable of growing on its own roots: 3 weeks.

Crop time: (from propagation to a saleable 1 gallon container): 6–10-weeks at temperatures of 75 degrees Fahrenheit–65 Fahrenheit.

Pest or disease susceptibility and resistance: No more or less susceptible to disease or pests than other cultivars.

Tuberous roots:

*Dimensions.*—5.0 inches in length, 2.75 inches in diameter. Color: 69B.

Foliage:

*Number.*—On average, a 5–6 month old mother plant maintains 5–6 functional leaves at a time, each new leaf is produced approximately every 10 days until the corm matures.

*Petioles.*—Length: Up to 82 cm in length. Width: 10 mm (just below attachment to lamina)×18 mm (upper sinus)×30 mm (at the middle of the sinus). Color: Mature leaf has a petiole color of N186C and younger leaves have petiole color of N77A. Sap color: red.

*Leaf.*—Dimensions at maturity (5–6 months old): 546 mm in length and 138 mm in width. Aspect: Erect with apex down. Shape: Sagittate lamina. Margins: Entire, undulating N186B. Apex: Pointed. Base: Peltate. Lamina appendages: Absent. Attachment: Petiolate with characteristic tissue formed at junction of leaf blade with the upper termination of the petiole. This area of the leaf tissue is also known as the "piko" and is evident by virtue of its upper surface being the same color as the veins or darker. The principal veins radiate from the piko. Piko color: N187A. Leaf sheaf: Open. Texture: Matte.

*Leaf color* (*adaxial surface*).—Younger leaf color 147A and older leaf 147B.

*Leaf color* (*abaxial surface*).—N77A.

*Venation.*—Palmate.

*Veins.*—Three principal veins radiating from the piko. The largest a midrib extending from the piko to the tip of the lamina with up to 11 pairs of secondary veins radiating from it.

*Vein color* (*adaxial surface*).—Younger leaf veins are 186C; mature leaf veins are 186B; older leaf veins are N186A.

*Vein color* (*abaxial surface*).—N186C.

Flowers and reproductive organs: The inflorescence arises from the leaf axils. The inflorescence is made up of a short peduncle, a spadix, and spathe. The spadix is botanically a spike, with a fleshy central axis to which the small sessile flowers are attached. The spadix is 265 mm to 305 mm long, with female flowers at the base, male flowers towards the tip, and sterile flowers in between, in the region compressed by the neck of the spathe. The extreme tip or appendage of the spadix has no flowers at all. The spathe is a large yellowish bract, 260 mm to 280 mm long, which sheathes the spadix. The lower part of the spathe is green (N186C) in color and wraps tightly around the spadix and completely occludes the female flowers from view. The top portion of the spadix is yellow (14D) in color and is rolled inward at the apex, but is open on one side to reveal the male flowers on the spadix. The top and bottom portions of the spadix are separated by a narrow neck region, corresponding to the region of the sterile flowers on the spadix.

Seed: Seed is not produced naturally since male and female flowers within each inflorescence do not mature at the same time. Pollination can be achieved manually or, in nature, only with the presence of small insect pollinators which are found in regions of genetic origin of the species, and not in Hawaii.

I claim:

1. A new and distinct cultivar of *Colocasia* plant named 'PINEAPPLE PRINCESS' as described and illustrated herein.

* * * * *

UNITED STATES PATENT AND TRADEMARK OFFICE

CERTIFICATE OF CORRECTION

PATENT NO. : PP20,982 P2
APPLICATION NO. : 12/006581
DATED : May 11, 2010
INVENTOR(S) : John Cho It is certified that error appears in the above-identified patent and that said Letters Patent is hereby corrected as shown below:

On Column 1, line 1, please insert the following header and paragraph:

--Statement of Government Interest

This invention was made with Government support under Grant No. 2001-31100-06015/HAW914H awarded by the U.S. Department of Agriculture. The Government has certain rights in this invention.--

Signed and Sealed this
Twenty-second Day of November, 2011

David J. Kappos

David J. Kappos
*Director of the United States Patent and Trademark Office*